United States Patent
Bradley

(10) Patent No.: US 6,652,503 B1
(45) Date of Patent: Nov. 25, 2003

(54) ABSORBENT SANITARY ARTICLE WITH POSTERIOR GUIDE RIDGE MEMBER

(76) Inventor: Ora Bradley, 6409 S. Honore St., Chicago, IL (US) 60636

(*) Notice: Subject to any disclaimer, the term of this patent is extended or adjusted under 35 U.S.C. 154(b) by 0 days.

(21) Appl. No.: 10/010,285

(22) Filed: Oct. 22, 2001

(51) Int. Cl.[7] ............................................. A61F 13/15
(52) U.S. Cl. ........................... 604/385.17; 604/385.01
(58) Field of Search .................. 604/385.01, 385.201, 604/385.17, 385.04, 385.05

(56) References Cited

U.S. PATENT DOCUMENTS

| | | |
|---|---|---|
| 3,998,447 A | 12/1976 | Joa |
| 4,681,578 A | 7/1987 | Anderson et al. |
| 4,699,823 A | 10/1987 | Kellenberger et al. |
| 4,804,380 A * | 2/1989 | Lassen et al. ............. 604/385.1 |
| 4,820,295 A | 4/1989 | Chapas et al. |
| 5,057,357 A * | 10/1991 | Winebarger ................. 428/195 |
| D358,207 S | 5/1995 | Glaug |
| 5,545,156 A | 8/1996 | DiPalma et al. |
| D393,712 S | 4/1998 | Clay |
| 6,100,442 A * | 8/2000 | Samuelsson et al. ....... 604/378 |
| D431,293 S | 9/2000 | Finkle et al. |
| 6,114,597 A * | 9/2000 | Romare ...................... 604/378 |
| 6,319,238 B1 * | 11/2001 | Sartorio et al. ............. 304/330 |
| 6,398,770 B1 * | 6/2002 | Drevik ................... 604/385.01 |

* cited by examiner

Primary Examiner—Aaron J. Lewis
Assistant Examiner—Jacqueline Stephens
(74) Attorney, Agent, or Firm—John D. Gugliotta; P. Jeff Martin

(57) ABSTRACT

An absorbent sanitary article with posterior guide ridge member is provided for effectively absorbing and retaining bodily fluid in the septum region of a wearer. The absorbent sanitary article with posterior guide ridge member has a bodycontacting surface for providing comfort against body skin and throughwhich bodily fluids will pass. An absorbency core provides some measure of bodily fluid absorbency. A barrier layer is included in order to prevent bodily fluids retained by the absorbency core from penetrating through the present invention and soiling adjacent undergarments. An outer layer imparts a degree of comfort and softness, as well as providing a vapor permeable sheathe. An integrally formed guide ridge is provided in order to be guidably received within a septum region of the wearer to prevent soilage of undergarments and to provide the wearer with a greater sense of dryness.

15 Claims, 5 Drawing Sheets

ABSORBENT SANITARY ARTICLE WITH POSTERIOR GUIDE RIDGE MEMBER

RELATED APPLICATIONS

The present invention was first described in a Disclosure Document Registration filed on Jun. 21, 2001, but not yet returned. There are no previously filed, nor currently any co-pending applications, anywhere in the world.

BACKGROUND OF THE INVENTION

1. Field of the Invention

The present invention relates generally to absorbent sanitary articles for absorbing body fluid and, more particularly, to an absorbent sanitary article with posterior guide ridge member.

2. Description of the Related Art

Many absorbent devices and articles including pantiliners and sanitary napkins are well known for their ability and use in absorbing and retaining body fluid discharges from the human body. These devices are typically employed during a woman's menstrual period to capture and retain menses and other vaginal discharges for preventing soilage of undergarments. While conventional devices such as pantiliners have been fairly efficient at best for controlling soilage to undergarments, none have addressed the common problem of gravitation of bodily fluid to a septum region of the body experienced when in a sitting or lying position, resulting in soilage to a rear portion of the undergarment and uncomfortable moisture next to the skin.

Accordingly, a need has arisen for a means by which to contain bodily fluid gravitation during a woman's menstrual cycle for preventing soiling of a rear area of an undergarment and which provides the wearer with a greater sense of dryness. The development of the absorbent sanitary article with posterior guide ridge member fulfills this need.

A search of the prior art did not disclose any patents that read directly on the claims of the instant invention; however, the following references were considered related. The following patents describe the function and design for various panty liners for use with thong underwear: U.S. Pat. No. 5,729,835 issued in the name of Williams; U.S. Pat. No. 5,713,886 issued in the name of Sturina; U.S. Pat. No. D 392,736 issued in the name of Erickson; U.S. Pat. No. D 366,529 issued in the name of Chung; U.S. Pat. No. D 352,351 issued in the name of Garth; U.S. Pat. No. D 276,184 issued in the name of Whitehead; and U.S. Pat. No. D 274,361 issued in the name of Whitehead.

U.S. Pat. No. 5,683,373 issued in the name of Darby discloses a sanitary napkin for use with a thong garment.

U.S. Pat. No. 5,545,156 issued in the name of DiPalma et al. discloses an absorbent article having a preformed member for close body contact.

U.S. Pat. No. D 240,564 issued in the name of Whitehead et al. discloses the ornamental design for a thin absorbent pad for a sanitary napkin.

Consequently, a need has been felt for providing a device which aids in preventing soiling of a rear area of an undergarment, and which provides the wearer with a greater sense of dryness in a manner which is quick, easy, and efficient.

SUMMARY OF THE INVENTION

Therefore, it is an object of the present invention to provide a sanitary article having a plurality of layers for absorbing and retaining bodily fluids.

It is another object of the present invention to provide a sanitary article having a rectangularly-shaped posterior portion for aiding in effective absorption and maintenance of bodily fluid.

It is another object of the present invention to provide a sanitary article with a structurally integral guide ridge for effectively absorbing and retaining bodily fluid in the septum region of a wearer.

It is another object of the present invention to provide a sanitary article with a bonding means for adhering to an upperside of a crotch portion of an undergarment.

It is another object of the present invention to provide a release liner for preventing undesired adhesion to extraneous surfaces prior to use.

It is still another object of the present invention to provide a pair of wings for aiding in maintaining the sanitary article in position during use.

Briefly described according to one embodiment of the present invention, an absorbent sanitary article with posterior guide ridge member is provided for effectively absorbing and retaining bodily fluid in the septum region of a wearer. The sanitary article is defined as having a bodycontacting surface for providing comfort against body skin and throughwhich bodily fluids will pass. The sanitary article further includes an absorbency core for providing some measure of bodily fluid absorbency. A barrier layer is provided in order to prevent bodily fluids retained by the absorbency core from penetrating through the sanitary article and soiling adjacent undergarments. An outer layer, lying just below the barrier layer, is provided in order to impart a degree of comfort and softness, as well as to provide a vapor permeable sheathe.

A seal, aligned along a periphery of the sanitary article, securably adjoins the bodycontacting surface, the absorbency core, the barrier layer, and the outer layer.

A bonding means is provided just below the barrier layer for adhering the present invention to an upperside of a crotch portion of an undergarment. A release liner serves to protect the bonding means by providing a cover thereover, thereby preventing undesired adhesion to extraneous surfaces prior to use.

A guide ridge is integrally formed along a longitudinal centerline of a rectangularly-shaped posterior portion of the posterior region. The guide ridge is designed and configured so as to be guidably received within a septum region of the wearer for functioning as a supplementary absorbency retainer for capturing bodily fluid gravitating toward the posterior portion of the posterior region. The rectangularly-shaped posterior portion in conjunction with the guide ridge facilitates effective absorption and maintenance of bodily fluid so as to prevent soilage of undergarments and to provide the wearer with a greater sense of dryness.

The use of the present invention aids in preventing soiling of a rear area of an undergarment, and provides the wearer with a greater sense of dryness in a manner which is quick, easy, and efficient.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 3 is a cross-sectional view of the central region of the present invention taken along lines III—III of FIG. 2a;

DESCRIPTION OF THE PREFERRED EMBODIMENT

1. Detailed Description of the Figures

Figure 1:
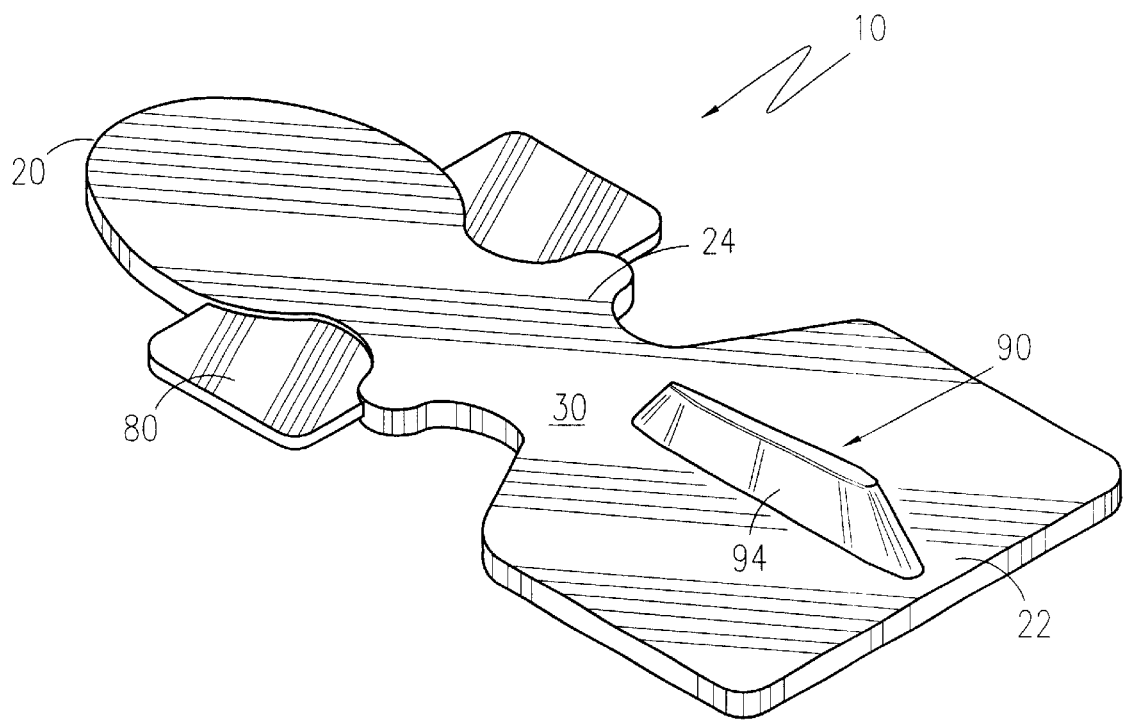
FIG. 1 is a perspective view of an absorbent sanitary article with posterior guide ridge member according to the preferred embodiment of the present invention.
Figure 2A:
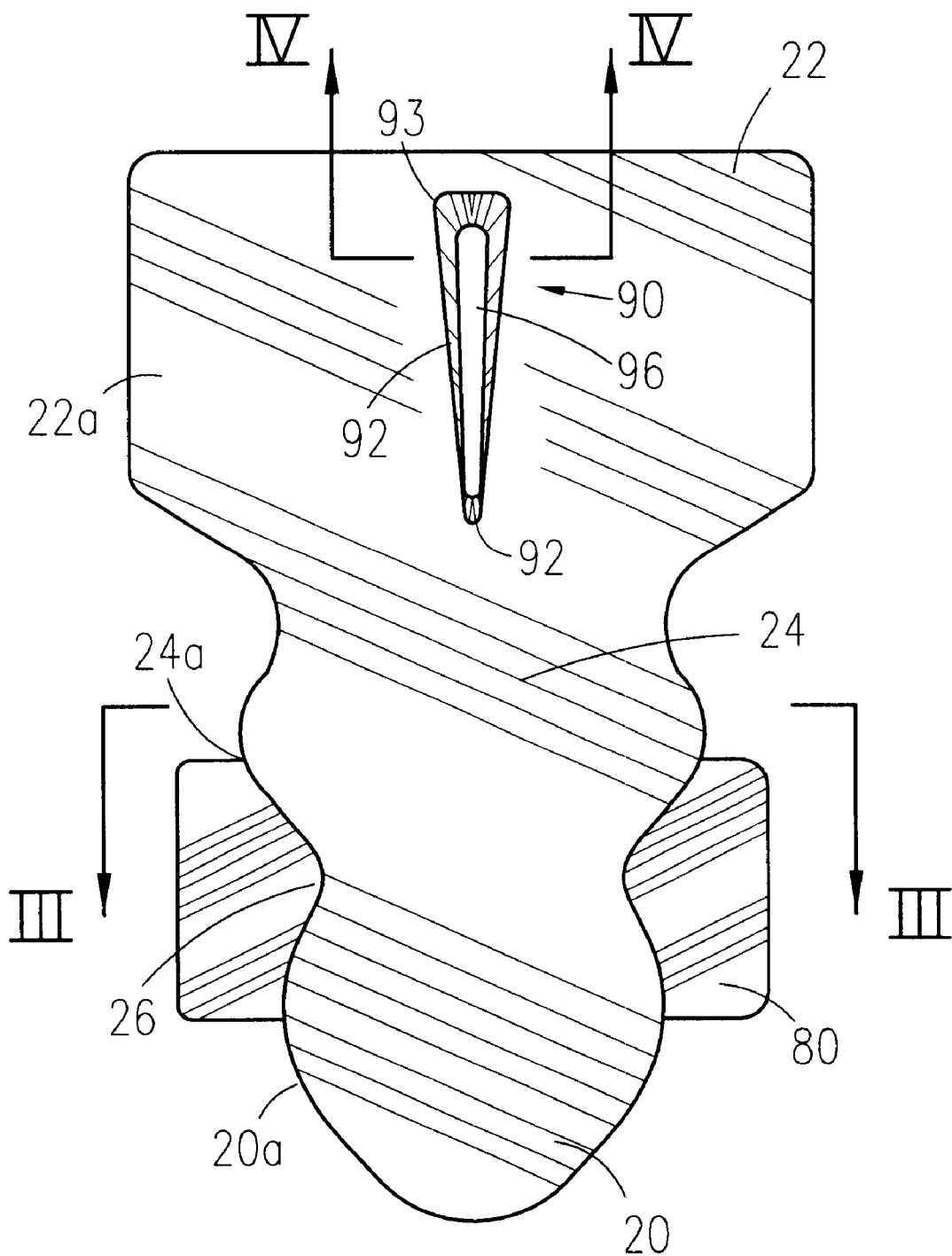
FIG. 2a is a top plan view thereof.
Figure 2B:
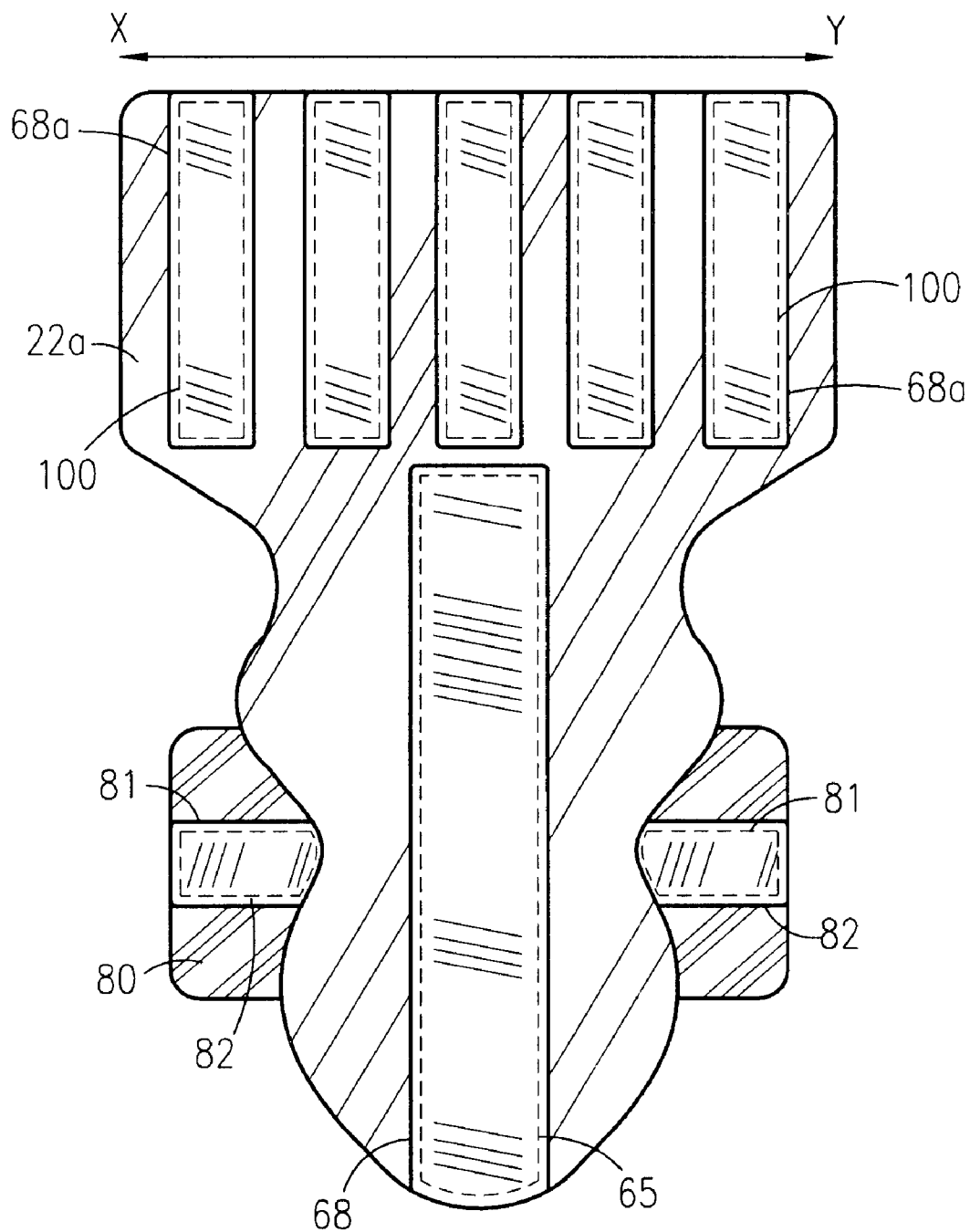
FIG. 2b is a bottom plan view thereof.
Figure 3:
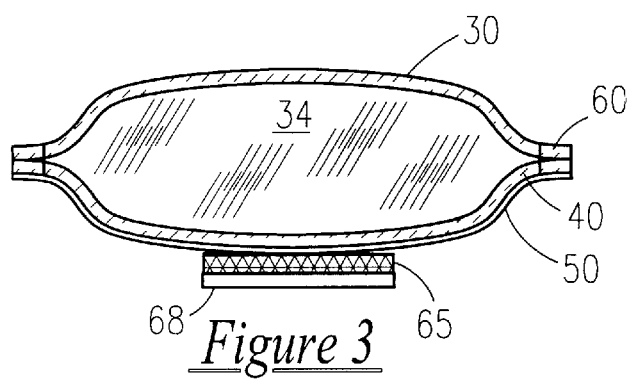
Figure 4:
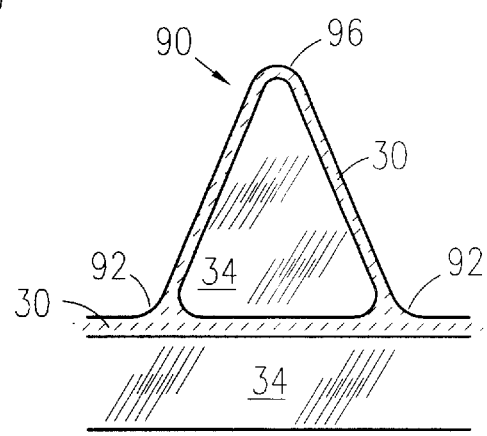
FIG. 4 is a cross-sectional view of the guide ridge taken along lines IV—IV of FIG. 2a according to the preferred embodiment of the present invention.
Figure 5:
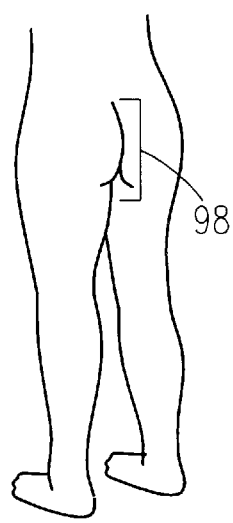
FIG. 5 is a perspective view of the septum region.

Referring now to FIGS. 1–5, an absorbent sanitary device 10 is shown, according to the present invention, comprised of an anterior region 20 opposite a posterior region 22, and a central region 24 located therebetween. The absorbent sanitary article with posterior guide ridge member 10, hereinafter referred to as sanitary article 10, has a shape being defined as tapering inward from a greater transverse width in anterior portion 20a of the anterior region 20 and central portion 24a of the central region 24 to a smaller transverse width at portion 26, and terminating to a substantially greater transverse width forming a generally rectangular shape at posterior portion 22a of the posterior region 22. The sanitary article 10 has a longitudinal length, as measured by a distance from the anterior region 20 to the posterior region 22, of approximately 11 inches. The posterior region 22 has a latitudinal width, as measured between points x and y shown in FIG. 2b, of approximately 8.5 to 9.0 inches. The sanitary article 10 is further defined as having a bodycontacting surface 30 for providing comfort against body skin and throughwhich bodily fluids will pass. The bodycontacting surface 30 is fabricated of a vapor and liquid-permeable material which functions to allow passage of bodily fluid therethrough so as to provide a surface being relatively dry next to bodily skin. Preferably, the bodycontacting surface 30 is fabricated of a fabric comprising heat bondable polyester/polyethylene conjugate fibers.

Underlying the bodycontacting surface 30 is an absorbency core 34 for providing some measure of bodily fluid absorbency. The absorbency core 34 is made of a composite of materials being substantially hydrophilic, adaptable, conformable, and non-irritating against wearer's skin. Suitable materials for fabrication are well known in the art, and include fluffed cellulose fibers, textile fibers, web of polymeric fibers, wood pulp fibers, polyester, polypropylene, polyurethane, cellulose sponge, and hydrophilic synthetic sponge.

In order to prevent bodily fluids retained by the absorbency core 34 from penetrating through the sanitary article 10 and soiling adjacent undergarments, a barrier layer 40 is provided. The barrier layer 40 is interposed between the absorbency core 34 and an outer layer 50 (to be described in greater detail below), and is fabricated of a suitably vapor and fluid impervious polymeric film material including polyethylene, cellophane, and polypropylene.

The outer layer 50 is provided in order to impart a degree of comfort and softness, as well as to provide a vapor permeable sheathe. The outer layer 50 lies just below the barrier layer 40 and is fabricated preferably of nonwoven materials.

In order to securably adjoin the bodycontacting surface 30, the absorbency core 34, the barrier layer 40, and the outer layer 50, a seal 60 is provided which is aligned along a periphery of the sanitary article 10. The seal 60 is produced by a method selected from the group consisting of thermal welding, ultrasonic welding, mechanical crimping, and adhesive bonding.

A bonding means 65 is provided just below the barrier layer 40 for adhering the sanitary article 10 to an upperside of a crotch portion of an undergarment. The bonding means 65 is comprised of a wide strip of suitably adhesive material extending a linear length from the anterior region 20 to just short of the posterior portion 22a of the posterior region 22. A release liner 68 serves to protect the bonding means 65 by providing a cover thereover, thereby preventing undesired adhesion to extraneous surfaces prior to use.

A series of linearly elongated, adhesive strips 100 is provided below the outer layer 50 of the rectangularly-shaped posterior portion 22a for aiding in adhering the sanitary article 10 to the upperside of a crotch portion of an undergarment. Each of the series of linearly elongated, adhesive strips 100 are provided with a release liner 68a.

A guide ridge member 90, integrally formed along a longitudinal centerline of the posterior portion 22a of the posterior region 20, affords important functional utility to the present invention described hereinbelow. The guide ridge member 90 is defined as being generally triangular in cross-section and has a base portion 92 with lateral sidewalls 94 converging slightly inward with increased distance from the base portion 92 which terminate to an apex 96. The lateral sidewalls 94 are further defined as diverging outwardly with increased distance from a forward portion 91 to a rearward portion 93 of the guide ridge member 90. The guide ridge member 90 includes an absorbency core 34 being fabricated of a composite of materials as described earlier. The absorbency core 34 is encapsulated by a bodycontacting surface 30, wherein the bodycontacting surface 30 is fabricated of a vapor or liquid-permeable material as described heretofore. The bodycontacting surface 30 along the base portion 92 of the guide ridge member 90 is in fluid communication with the bodycontacting surface 30 of the sanitary article 10 along the longitudinal centerline of the posterior portion 22a of the posterior region 20 thereof. The guide ridge 90 is designed and configured so as to extend approximately 0.5 inches to 1.0 inch above the base portion 92 and to have a length measuring approximately 4.0 inches to 5.0 inches so as to be guidably received within a septum region 98 of the wearer.

Soiling of the posterior area of an undergarment is further prohibited by the unique rectangular design of the posterior portion 22a of the posterior region 20. The posterior portion 22a provides sufficient surface area for effectively absorbing and restraining excess bodily fluid encountered therewith. Thus, the combination of the guide ridge member 90 and the posterior portion 22a provide a unique design for facilitating absorption of bodily fluid having gravitated to the posterior portion 22a of the posterior region of the sanitary article 10, so as to not only prevent soilage of undergarments, but also to enhance movements of body fluids penetrating the guide ridge 90 and posterior portion 22a away from the wearer, thereby providing the wearer with a greater sense of dryness in the septum region 98.

A pair of wings 80 is provided wherein each extends laterally of portion 26 at opposed sides thereof, and which reside just below the seal 60. Each of the pair of wings 80 are designed and configured to extend generally over edges of an undergarment and adhere to an underside of the crotch portion thereof. Each of the pair of wings 80 has an adhesive strip 81 located on an underside thereof to facilitate adhesion. A release liner 82 serves to protect each adhesive strip 81 by providing a cover thereover, thereby preventing undesired adhesion to extraneous surfaces prior to use. The wings 80 function to further aid in maintaining the sanitary article 10 in position during use.

Figure 6:
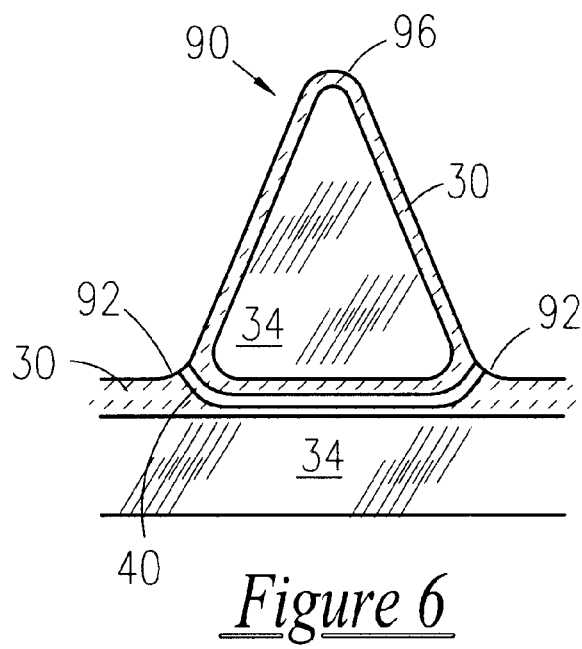
FIG. 6 illustrates a first alternate embodiment of the present invention.

Referring now to FIG. 6, a first alternate embodiment of the present invention is shown, wherein a barrier layer 40 is interposed between the absorbency core 34 and body contacting surface 30 of the guide ridge member 90 along the base portion 92 thereof. The barrier layer 40 is fabricated of a suitably vapor and fluid impervious polymeric film material as previously described.

Figure 7:
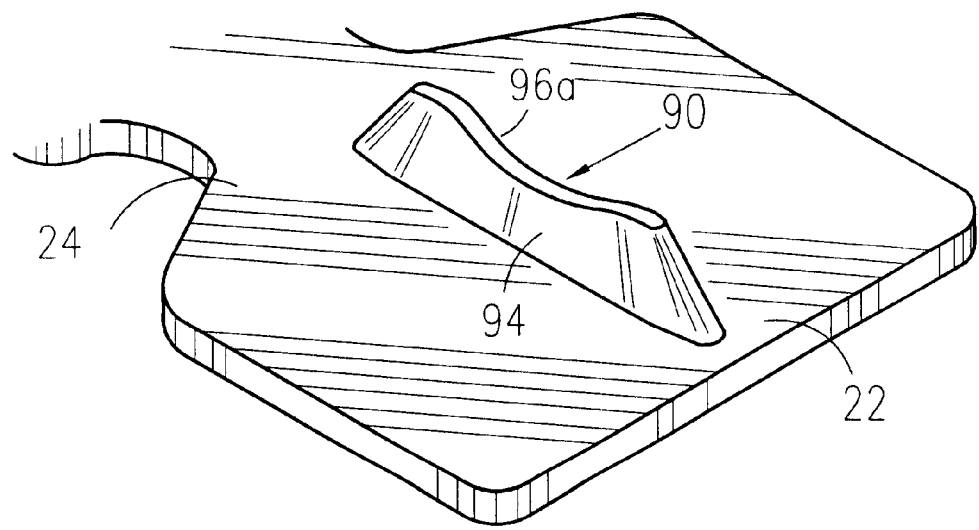
FIG. 7 illustrates a second alternate embodiment of the present invention.

Finally, referring to FIG. 7, a second alternate embodiment of the present invention is shown, wherein the guide ridge member 90 is defined as having a concave-shaped apex 96a. The concave-shaped apex 96a facilitates biomechanical conformation of the guide ridge member 90 with the septum region 98, thereby providing the wearer with added comfort during use.

2. Operation of the Preferred Embodiment

To use the present invention, the user removes the release liners 68, 68a from both the bonding means 65 and adhesive strips 100, respectively, and adheres an underside of the sanitary article 10 to an upperside of a crotch portion of an undergarment. The user then removes the release liner 82 from the wings 80 and extends them over edges of the undergarment where the wings 80 are adhered to an underside of the crotch portion to aid in maintaining the sanitary article 10 in position during use. Next, as the user pulls the undergarment with adhered sanitary article 10 up near the crotch region, the user carefully allows the guide ridge member 90 to be guidably inserted within the septum region 98. The sanitary article 10 is disposed of after use.

The use of the present invention aids in preventing soiling of a rear area of an undergarment, and provides the wearer with a greater sense of dryness in a manner which is quick, easy, and efficient.

Therefore, the foregoing description is included to illustrate the operation of the preferred embodiment and is not meant to limit the scope of the invention. As one can envision, an individual skilled in the relevant art, in conjunction with the present teachings, would be capable of incorporating many minor modifications that are anticipated within this disclosure. Therefore, the scope of the invention is to be broadly limited only by the following claims.

What is claimed is:

1. An absorbent sanitary device comprising:
    a sanitary article, said sanitary article having an anterior region located opposite a posterior region, and wherein said sanitary article having a central region located between said anterior region and said posterior region; said sanitary article has a shape being defined as tapering inward from a greater transverse width in an anterior portion of said anterior region and a central portion of said central region to a smaller transverse width, and terminating to a substantially greater transverse width forming a posterior portion having a generally rectangular shape, and wherein said posterior portion having sufficient surface area for preventing soilage of undergarments and providing wearer with a sense of dryness in said septum region;
    a guide ridge member, said guide ridge member being generally triangular in cross-section;
    a seal, said seal is aligned along a periphery of said sanitary article;
    a bonding means, said bonding means is defined as a wide strip of suitably adhesive material; and
    a pair of wings, said pair of wings being designed and configured so as to extend generally over edges of an undergarment and adhere, via adhesive strips located on a bottom of said pair of wings, to an underside of a crotch portion of the undergarment.

2. The absorbent sanitary device of claim 1, wherein said sanitary article has a bodycontacting surface for providing comfort against body skin and throughwhich bodily fluids will pass, and wherein said bodycontacting surface is fabricated of a vapor and liquid-permeable material.

3. The absorbent sanitary device of claim 2, wherein said bodycontacting surface of said sanitary article is fabricated of a fabric material comprising heat bondable polyester/polyethylene conjugate fibers.

4. The absorbent sanitary device of claim 2, wherein said sanitary article has an absorbency core underlying said bodycontacting surface, and wherein said absorbency core is fabricated of a composite of materials being substantially hydrophilic, adaptable, conformable, and non-irritating against body skin for providing some measure of bodily fluid absorbency.

5. The absorbent sanitary device of claim 4, wherein said absorbency core is fabricated of materials selected from members of the group consisting of fluffed cellulose fibers, textile fibers, web of polymeric fibers, wood pulp fibers, polyester, polypropylene, polyurethane, cellulose sponge, and hydrophilic synthetic sponge.

6. The absorbent sanitary device of claim 4, wherein said sanitary article has a barrier layer interposed between said absorbency core and an outer layer for preventing bodily fluids retained by said absorbency core from penetrating through said sanitary article and soiling adjacent undergarments, said barrier layer is fabricated of a suitably vapor and fluid impervious polymeric film material, and wherein said outer layer has a series of linearly elongated, adhesive strips aligned thereunder along said posterior portion, and wherein each adhesive strip of said series of linearly elongated, adhesive strips is overlapped by a release liner for preventing undesired adhesion of said series of linearly elongated, adhesive strips to extraneous surfaces prior to use.

7. The absorbent sanitary device of claim 6, wherein said barrier layer is fabricated of a material selected from a member of the group consisting of polyethylene, cellophane, and polypropylene.

8. The absorbent sanitary device of claim 6, wherein said outer layer lies just below said barrier layer and is fabricated of nonwoven materials in order to impart a degree of comfort and softness and to provide a sheathe being vapor permeable.

9. The absorbent sanitary device of claim 8, wherein said bodycontacting surface, said absorbency core, said barrier layer, and said outer layer are securably adjoined by said seal, wherein said absorbency core is effectively crimped integral to said seal.

10. The absorbent sanitary device of claim 9, wherein said seal is produced by a method selected from the group consisting of thermal welding, ultrasonic welding, mechanical crimping, and adhesive bonding.

11. The absorbent sanitary device of claim 8, wherein said barrier layer has said bonding means located just below said barrier layer for adhering said sanitary article to an upperside of the crotch portion of the undergarment, and wherein said bonding means extends a linear length from said anterior region to just short of said posterior portion of said posterior region.

12. The absorbent sanitary device of claim 11, wherein said bonding means is overlapped by a release liner for preventing undesired adhesion of said bonding means to extraneous surfaces prior to use.

13. The absorbent sanitary device of claim 1, wherein said guide ridge member is integrally formed along a longitudinal centerline of said posterior portion of said posterior region, said guide ridge member has a base portion with lateral sidewalls converging slightly inward with increased distance from said base portion which terminate to an apex, and said lateral sidewalls diverging outwardly with increased distance from a forward portion of said guide ridge to a rearward portion of said guide ridge member.

14. The absorbent sanitary device of claim 13, wherein said guide ridge member includes an absorbency core encapsulated by a bodycontacting surface, and wherein said bodycontacting surface is in fluid communication with said bodycontacting surface of said sanitary article.

15. The absorbent sanitary device of claim 14, wherein said guide ridge member extends approximately 0.5 inches to 1.0 inches above said base portion and has a length measuring approximately 4.0 inches to 5.0 inches so as to be guidably received within a septum region of wearer, thereby preventing soilage of undergarments and providing wearer with a sense of dryness in said septum region.

\* \* \* \* \*